US010226288B2

(12) United States Patent
Sidebotham et al.

(10) Patent No.: US 10,226,288 B2
(45) Date of Patent: Mar. 12, 2019

(54) OSTEOTOMY PLATE FOR LONG BONES

(71) Applicant: BioMedtrix, LLC, Whippany, NJ (US)

(72) Inventors: Christopher G. Sidebotham, Boonton, NJ (US); Gregory Thomas Van Der Meulen, Ketchum, ID (US); Randall Lane Acker, Ketchum, ID (US)

(73) Assignee: BioMedtrix, LLC, Whippany, NJ (US)

( * ) Notice: Subject to any disclaimer, the term of this patent is extended or adjusted under 35 U.S.C. 154(b) by 343 days.

(21) Appl. No.: 14/936,556

(22) Filed: Nov. 9, 2015

(65) Prior Publication Data

US 2016/0128745 A1 May 12, 2016

Related U.S. Application Data

(60) Provisional application No. 62/077,704, filed on Nov. 10, 2014.

(51) Int. Cl.
*A61B 17/80* (2006.01)
*A61D 1/00* (2006.01)

(52) U.S. Cl.
CPC ...... *A61B 17/8014* (2013.01); *A61B 17/8057* (2013.01); *A61B 17/8095* (2013.01); *A61D 1/00* (2013.01)

(58) Field of Classification Search
CPC .................. A61B 17/8014; A61B 17/8095
See application file for complete search history.

(56) References Cited

U.S. PATENT DOCUMENTS 5,718,705 A * 2/1998 Sammarco ......... A61B 17/8085
606/260

| 8,523,921 | B2 | 9/2013 | Horan et al. | |
| 9,907,588 | B2 * | 3/2018 | Parekh | A61B 17/8014 |
| 2005/0015089 | A1 * | 1/2005 | Young | A61B 17/8014 606/915 |
| 2005/0240187 | A1 * | 10/2005 | Huebner | A61B 17/80 606/71 |
| 2005/0261688 | A1 * | 11/2005 | Grady, Jr. | A61B 17/8014 606/286 |
| 2006/0129151 | A1 * | 6/2006 | Allen | A61B 17/8014 606/281 |
| 2006/0235396 | A1 * | 10/2006 | Sanders | A61B 17/8061 606/280 |

(Continued)

OTHER PUBLICATIONS

Document entitled "Bone Plates" illustrating various tibial bone plates, femoral bone plates, and humeral bone plates, along with the manufacturer, where known. 3 pp. Each of the bone plates shown in the "Bone Plates" document is understood to have been publicly available before Nov. 10, 2014, the priority date of the present application.

*Primary Examiner* — David W Bates
(74) *Attorney, Agent, or Firm* — Klarquist Sparkman, LLP

(57) ABSTRACT

A bone plate has a curved elongated body including a first end portion and a second end portion. The first end portion is laterally offset relative to the second end portion, and includes a plurality of screw holes. A first screw hole is defined by the second end portion. Each of the screw holes of the first end portion are laterally offset from a straight line extending in a direction along a length dimension of the bone plate and bisecting the first screw hole of the second end portion, and each of the screw holes of the first end portion are on the same side of the straight line as one another.

19 Claims, 12 Drawing Sheets

(56) References Cited

U.S. PATENT DOCUMENTS

| | | | |
|---|---|---|---|
| 2007/0233106 A1* | 10/2007 | Horan | A61B 17/8061 606/282 |
| 2008/0281327 A1* | 11/2008 | Helfteren | A61B 17/8071 606/71 |
| 2009/0143825 A1* | 6/2009 | Graham | A61B 17/8014 606/286 |
| 2009/0306724 A1* | 12/2009 | Leither | A61B 17/8057 606/289 |
| 2010/0030276 A1* | 2/2010 | Huebner | A61B 17/8061 606/280 |
| 2010/0121325 A1* | 5/2010 | Tyber | A61B 17/1717 606/62 |
| 2010/0274293 A1* | 10/2010 | Terrill | A61B 17/8057 606/286 |
| 2012/0059424 A1* | 3/2012 | Epperly | A61B 17/8061 606/281 |
| 2012/0265254 A1 | 10/2012 | Horan et al. | |
| 2012/0265255 A1* | 10/2012 | Hilse | A61B 17/8014 606/290 |
| 2013/0238032 A1* | 9/2013 | Schilter | A61B 17/80 606/281 |
| 2014/0180343 A1* | 6/2014 | Gaudin | A61B 17/8061 606/283 |
| 2015/0127011 A1* | 5/2015 | Dunlop | A61B 17/80 606/88 |
| 2016/0199110 A1* | 7/2016 | Austin | A61B 17/8061 606/281 |
| 2016/0256204 A1* | 9/2016 | Patel | A61B 17/8014 |
| 2016/0310184 A1* | 10/2016 | Kazanovicz | A61B 17/8061 |
| 2016/0310185 A1* | 10/2016 | Sixto | A61B 17/8061 |
| 2017/0056081 A1* | 3/2017 | Langdale | A61B 17/8061 |
| 2018/0049787 A1* | 2/2018 | Davison | A61B 17/8085 |

\* cited by examiner

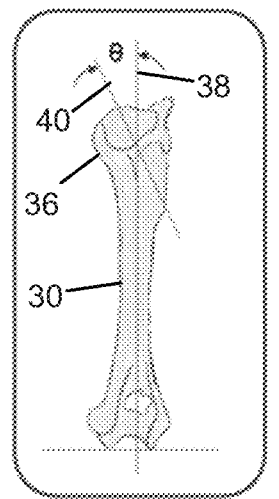 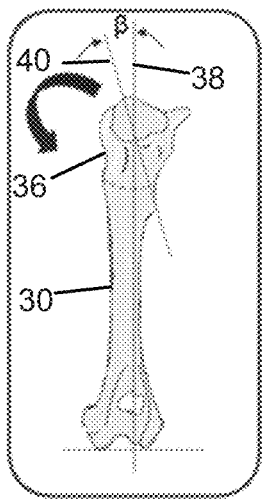 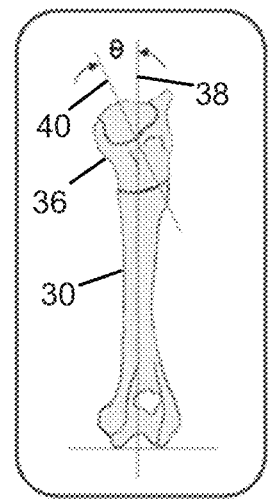
FIG. 8A  FIG. 8B  FIG. 8C
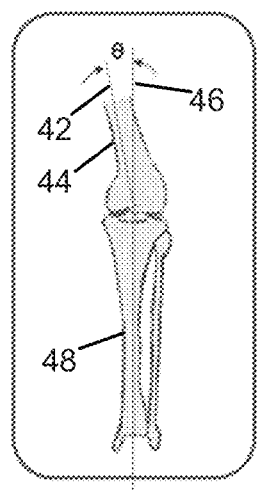 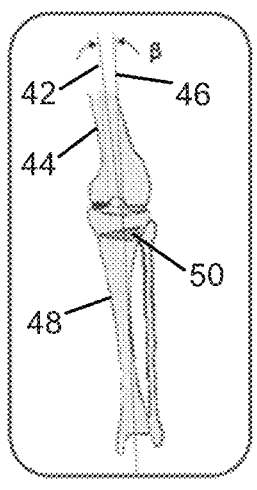 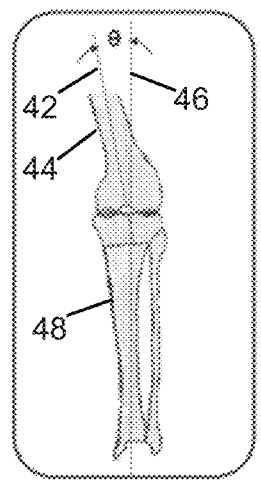
FIG. 9A  FIG. 9B  FIG. 9C

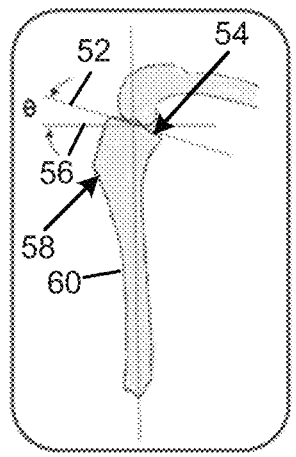 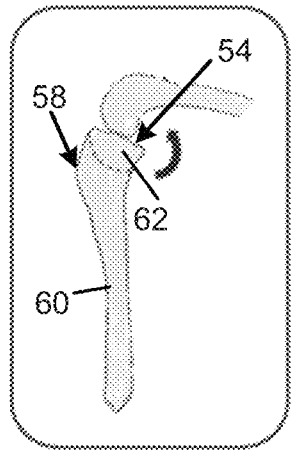 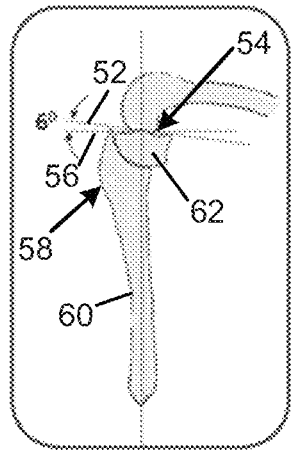
FIG. 10A  FIG. 10B  FIG. 10C
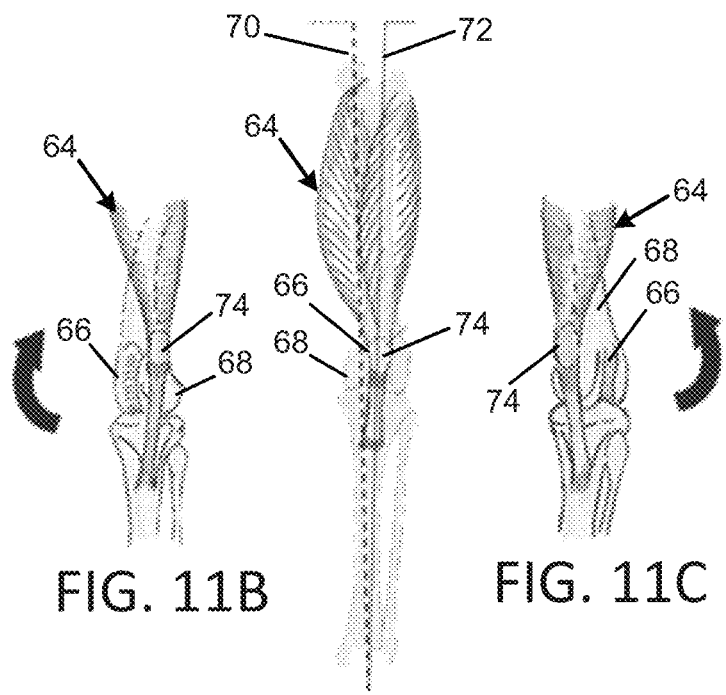
FIG. 11B  FIG. 11C
FIG. 11A

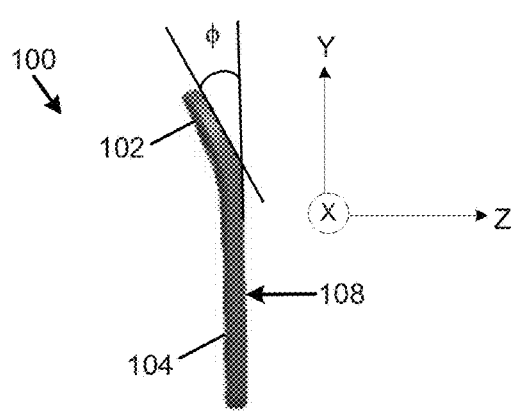
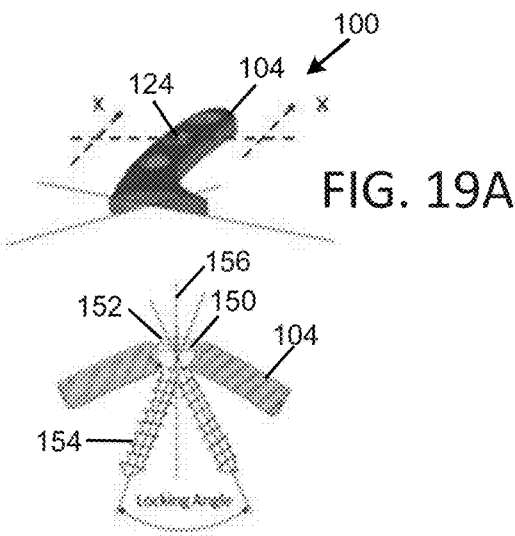
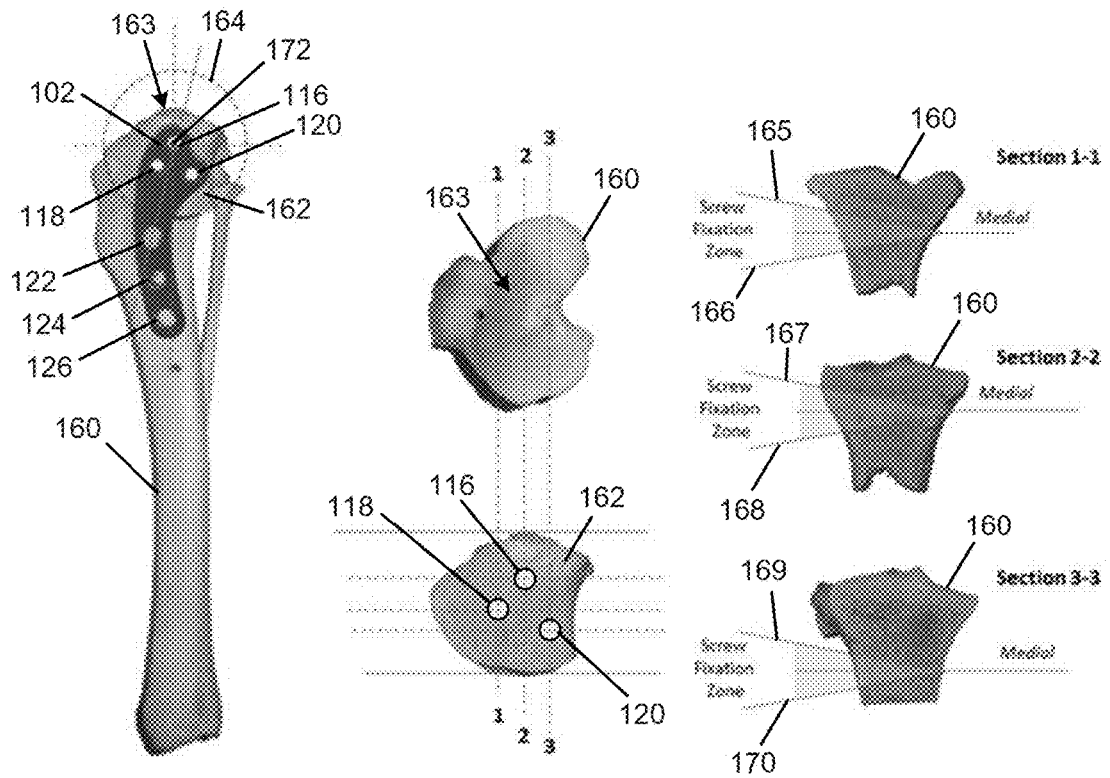
FIG. 18  FIG. 19A  FIG. 19B  FIG. 20A  FIG. 20B  FIG. 20C

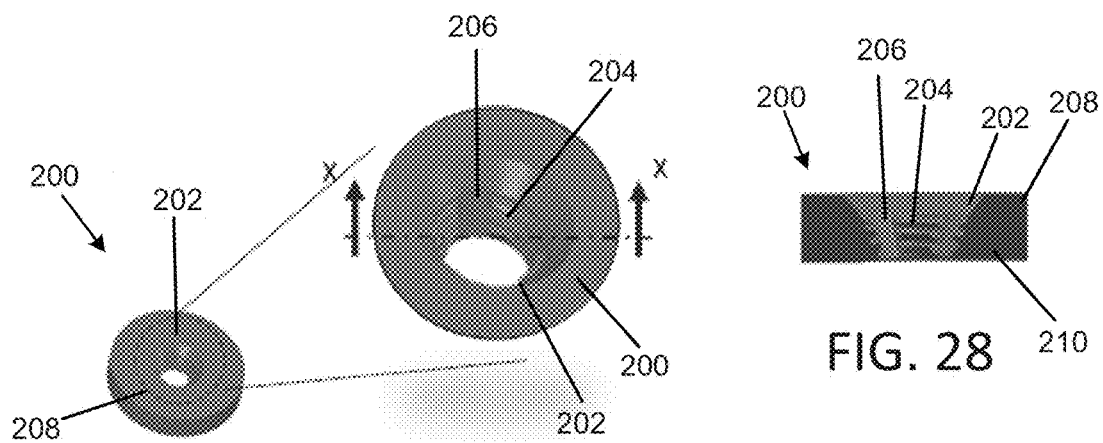
FIG. 27
FIG. 28
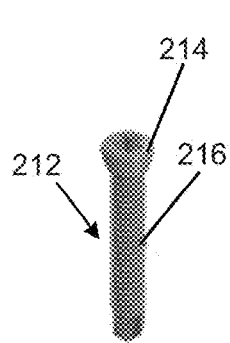
FIG. 29
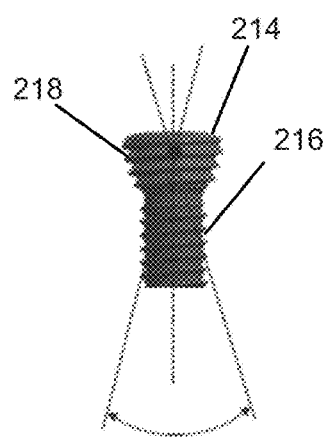
FIG. 30

OSTEOTOMY PLATE FOR LONG BONES

CROSS REFERENCE TO RELATED APPLICATION

This application claims the benefit of U.S. Provisional Patent Application No. 62/077,704, filed Nov. 10, 2014, which is hereby incorporated herein by reference in its entirety.

FIELD

This disclosure pertains to bone plates and associated methods of use.

BACKGROUND

In osteotomy procedures, it is often advantageous for a bone plate to provide stabilization of the osteotomy site and compression of the osteotomy. When adequate stability is not achieved, the bone segment(s) may move, resulting in inferior biomechanics due to deviation from the planned alignment. Lack of compression at the osteotomy interface can also result in delayed or non-union outcomes. Many conventional bone plates also necessitate a multitude of plate designs in multiple sizes and orientations to address various clinical indications in bones, complicating bone plate selection and use. Accordingly, improvements to bone plates are desirable.

SUMMARY

Certain embodiments of the disclosure concern bone plates for use with long bones. In an exemplary embodiment, a bone plate comprises a curved elongated body including a first end portion and a second end portion. The first end portion is laterally offset relative to the second end portion. The bone plate further includes a plurality of screw holes defined by the first end portion, and a first screw hole defined by the second end portion. Each of the screw holes of the first end portion are laterally offset from a straight line extending in a direction along a length dimension of the bone plate and bisecting the first screw hole of the second end portion, and each of the screw holes of the first end portion are on the same side of the straight line as one another.

In another representative embodiment, a bone plate comprises an elongated body including a first end portion and a second end portion. The elongated body defines an upper surface and a lower surface, and has a V-shaped cross section. The elongated body is curved such that the first end portion is laterally offset relative to the second end portion. The bone plate further includes a plurality of screw holes defined by the first end portion and a plurality of screw holes defined by the second end portion, at least one of the screw holes of the second end portion being a first compression screw hole oriented such that a straight line extending along a longitudinal axis of the first compression screw hole passes through a proximal screw hole of the first end portion.

In another representative embodiment, a method comprises placing a bone plate on an end portion of a long bone. The bone plate includes a curved elongated body having a first end portion and a second end portion. The first end portion is laterally offset relative to the second end portion, and the first end portion defines a plurality of screw holes. The second end portion defines at least one screw hole, and each of the screw holes of the first end portion are laterally offset from a straight line extending in a direction along a length dimension of the bone plate and bisecting the at least one screw hole of the second end portion. Each of the screw holes of the first end portion are on the same side of the straight line as one another. The method further comprises securing the bone plate to the long bone.

The foregoing and other objects, features, and advantages of the disclosed technology will become more apparent from the following detailed description, which proceeds with reference to the accompanying figures.

BRIEF DESCRIPTION OF THE DRAWINGS

FIGS. 8A-8C illustrate a representative proximal humeral version correction procedure.

FIGS. 9A-9C illustrate a representative high tibial osteotomy procedure.

FIGS. 10A-10C illustrate a representative tibial plateau leveling osteotomy (TPLO) procedure.

FIGS. 11A-11C illustrate medial and lateral patellar luxation.

FIG. 18 is a side elevation view of the bone plate of FIG. 14 illustrating the angle of the first end portion relative to the second end portion.

FIG. 19A is an end view of the bone plate of FIG. 14.

FIG. 19B is a cross-sectional view of the bone plate taken along line X-X of FIG. 19A illustrating the angles at which a bone screw may be inserted through a screw hole.

FIGS. 20A-20C illustrate the location and range of angles at which bone screws may be inserted into a bone segment through the screw holes of the first end portion of the bone plate of FIG. 14 in a TPLO procedure.

FIGS. 27 and 28 illustrate another embodiment of a locking screw hole that can be used in combination with any of the bone plates described herein.

FIGS. 29 and 30 illustrate a representative embodiment of a locking screw.

DETAILED DESCRIPTION

Figure 1:
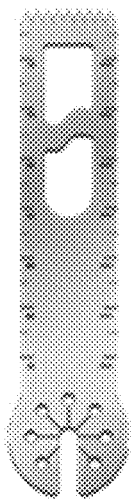
FIGS. 1-3 are representative examples of saw blades that can be used in the osteotomy procedures described herein.
Figure 2:
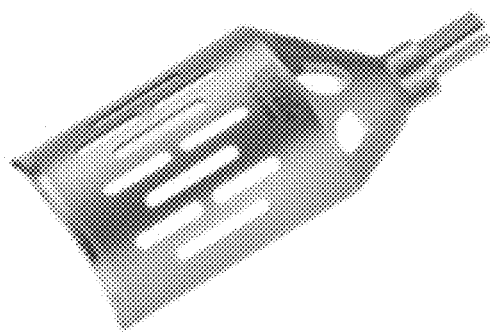
Figure 3:
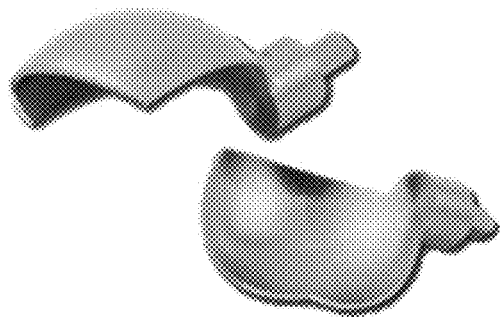

In human and animal orthopedics, various saw blades are available to make osteotomies in bone. Straight osteotomies, radial osteotomies, and spherical osteotomies can be created at specific locations in long bones to achieve realignment of a bone segment to the overall limb axis for improved biomechanics. Representative examples of a flat saw blade, a radial saw blade, and a spherical or dome saw blade are shown in FIGS. 1-3, respectively.

There are multiple physiological problems associated with long bones that can affect limb biomechanics, which can occur as a result of trauma (e.g., bone fractures that heal in a misaligned position), or birth defects. Surgical methods of re-establishing appropriate biomechanics of a limb can include repositioning proximal and distal bone segments to correct alignment issues. There are clinical examples for many long bones (e.g., femur, tibia, humerus, radius, ulna, etc.), which can be managed through corrective osteotomies to restore improved limb function. With reference to the femur, there are proximal and distal corrective osteotomies that can address different biomechanical alignment issues.

Figure 4A:
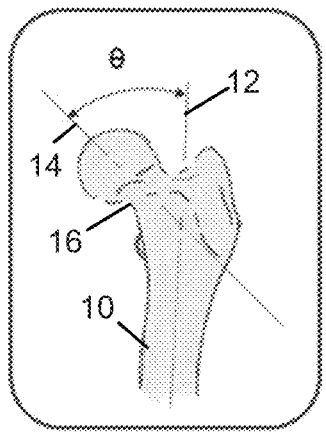
FIGS. 4A-4C illustrate a representative femoral neck angle correction procedure.
Figure 4B:
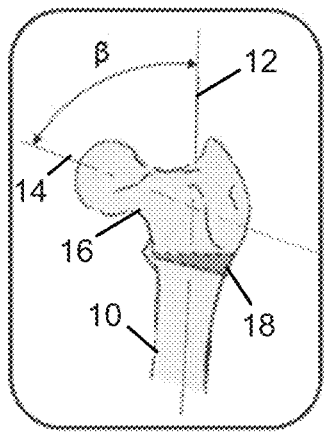
Figure 4C:
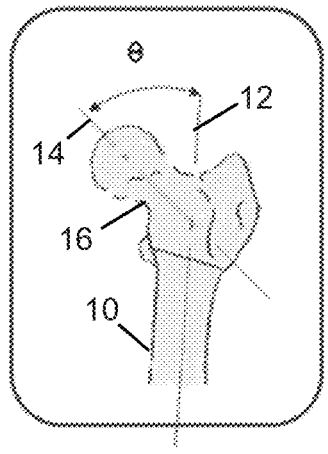

For example, a representative femoral neck angle correction is shown in FIGS. 4A-4C. FIG. 4A illustrates a normal angle θ between a longitudinal axis 12 of a femur 10 and a longitudinal axis 14 of the femoral neck 16. FIG. 4B illustrates a case in which the angle β between the longitudinal axis 12 of the femur and the longitudinal axis 14 of the femoral neck is greater than normal. The angle of the femoral neck can be corrected by performing an osteotomy (e.g., with flat saw blade) to remove a wedge-shaped portion 18 of the femur (FIG. 4B) to locate the femoral neck at the desired angle θ (FIG. 4C).

Figure 5A:
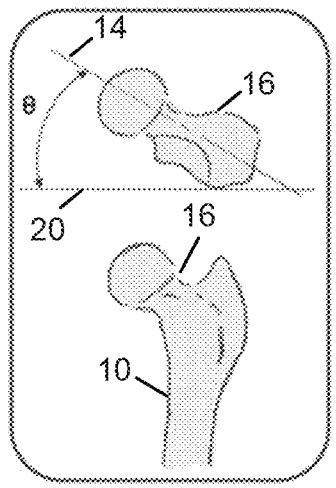
FIGS. 5A-5C illustrate a representative femoral version correction procedure.
Figure 5B:
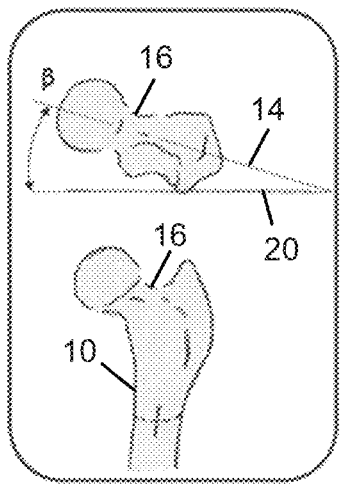
Figure 5C:
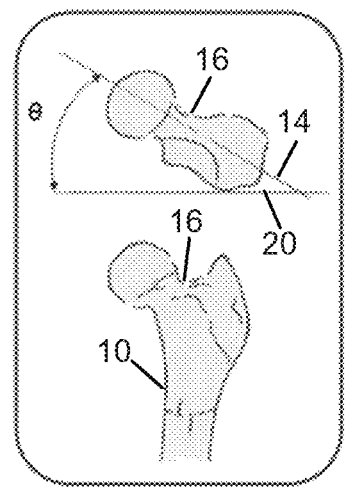

A representative femoral version correction is shown in FIGS. 5A-5C, wherein the femoral anteversion angle θ between the longitudinal axis 14 of the femoral neck 16 is corrected relative to a horizontal plane 20. FIG. 5A illustrates a normal femoral anteversion angle θ, while FIG. 5B illustrates a femoral anteversion angle β that is less than normal. By performing an osteotomy (e.g., with a flat saw blade) to rotate the femoral neck 16, the anteversion angle can be corrected, as shown in FIG. 5C.

Figure 6A:
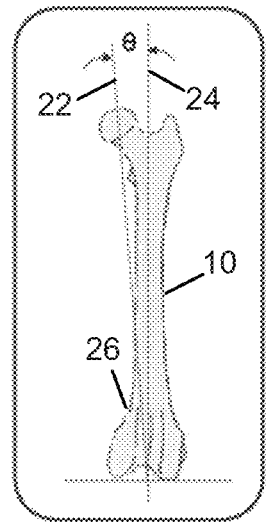
FIGS. 6A-6C illustrate a representative distal femoral loading angle correction procedure.
Figure 6B:
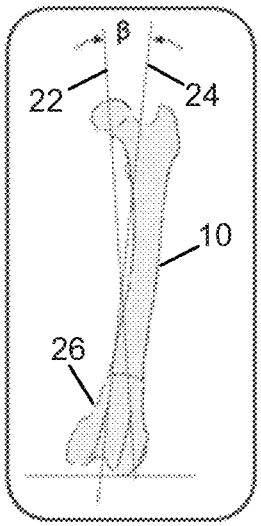
Figure 6C:
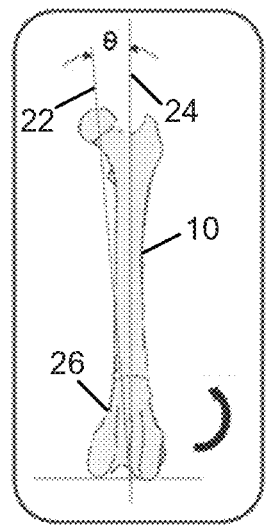

A representative distal femoral loading angle correction is shown in FIGS. 6A-6C. FIG. 6A illustrates a normal femoral loading angle θ between a loading axis 22 and an anatomical axis 24, while FIG. 6B illustrates an abnormal loading angle β. By performing an osteotomy (e.g., with a radial saw blade) to rotate a distal end portion 26 of the femur 10, the loading angle can be corrected, as shown in FIG. 6C.

Figure 7A:
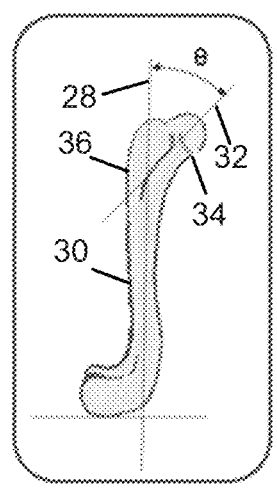
FIGS. 7A-7C illustrate a representative humeral neck angle correction procedure.
Figure 7B:
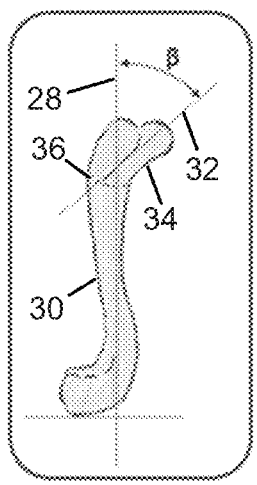
Figure 7C:
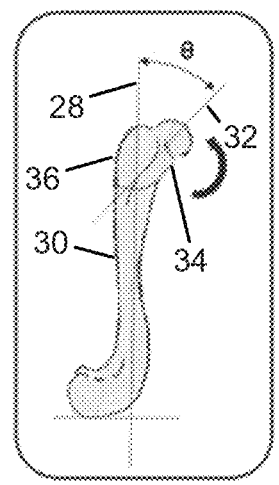

There can be similar clinical issues with the humerus, as illustrated in FIGS. 7A-7C and 8A-8C. For example, FIGS. 7A-7C illustrate a representative humeral neck angle correction, with a normal humeral neck angle θ between a longitudinal axis 28 of the humerus 30 and a longitudinal axis 32 of the humeral neck 34 shown in FIG. 7A, and an abnormal humeral neck angle β illustrated in FIG. 7B. By performing an osteotomy to rotate a proximal portion 36 of the humerus 30, the neck angle can be corrected, as illustrated in FIG. 7C.

FIGS. 8A-8C illustrate a representative proximal humeral version correction, with a head-neck angle θ between a longitudinal axis 38 of the humerus 30 and an axis 40 of the proximal humerus 36 shown in FIG. 8A, and an abnormal humeral version angle β shown in FIG. 8B. By performing an osteotomy to rotate the proximal portion 36 of the humerus 30 in the manner indicated, the humeral version angle can be corrected, as shown in FIG. 8C.

Osteotomies of the tibia can involve plateau positional changes to correct over-loading of areas of the articular surface (e.g., surfaces with cartilage). In humans, a high tibial osteotomy (HTO) can be performed to balance the loading in both compartments of the knee, as shown in FIGS. 9A-9C. FIG. 9A illustrates a normal femuro-tibial loading angle θ between a loading axis 42 of a femur 44 and a longitudinal axis 46 of a tibia 48 wherein about 60% of the load applied by the femur is borne by the medial aspect of proximal tibia and about 40% of the load is borne by the lateral aspect of the proximal tibia. FIG. 9B illustrates the case of an abnormal femuro-tibial loading angle β wherein, in some examples, about 80% of the load applied by the femur can be borne by the medial aspect of the tibia and only about 20% of the load can be borne by the lateral aspect of the tibia. The angle β can be corrected by performing an osteotomy to remove a wedge-shaped portion 50 of the proximal tibia (FIG. 9B) to restore a normal femuro-tibial loading angle θ, as illustrated in FIG. 9C.

In veterinary medicine, a tibial plateau leveling osteotomy (TPLO) can be performed to re-position the tibial plateau to, for example, function as a buttress to resist certain physiological movements or address rupture of the anterior (cranial) cruciate ligament. FIGS. 10A-10C illustrate a representative example of a TPLO procedure. FIG. 10A illustrates a normal angle θ between a plane 52 defined by the tibial plateau 54 and a horizontal reference plane 56. In certain circumstances, it can be beneficial to rotate the plane 52 of the tibial plateau 54 to reduce the angle between the tibial plateau and the reference plane 56. This can be accomplished by creating a radial cut in a proximal portion 58 of the tibia 60 and rotating the excised portion 62 such that the angle between the tibial plateau 54 and the horizontal reference plane 56 is lowered (e.g., to about 6 degrees in some embodiments), as shown in FIGS. 10B and 10C.

Patellar luxation is another example of a pathology that may be addressed by osteotomy procedures. With reference to FIGS. 11A-11C, patellar luxation can occur when there is a misalignment between the quadriceps mechanism generally indicated at 64 and the trochlear groove 66 of the distal femur 68, and/or when there is a disparity between the loading axis 70 of the leg and the anatomical axis 72, as illustrated in FIG. 11A. In such circumstances, when the knee is flexed, the patella 74 can travel out of the trochlear groove 66, or luxate, resulting in pain and limited motion and function. Lateral luxation of the patella 74 is illustrated in FIG. 11B, while medial luxation is illustrated in FIG. 11C. By performing a distal femoral correction osteotomy in the manner of FIGS. 6A-6C, the distal aspect of the femur 68 can be realigned with the pull of the quadriceps 64 to re-establish alignment, stability, and function.

Figure 12A:
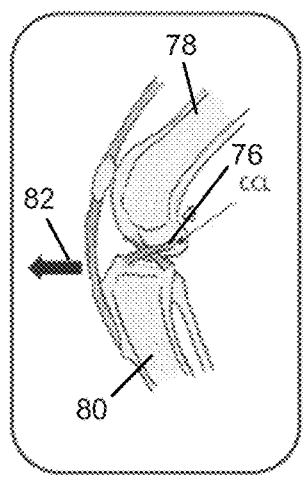
FIGS. 12A-12C illustrate a representative repair of a ruptured cranial cruciate ligament by performing a TPLO.
Figure 12B:
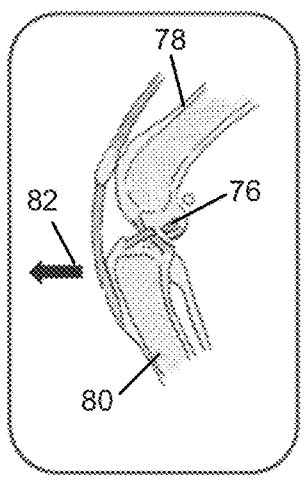
Figure 12C:
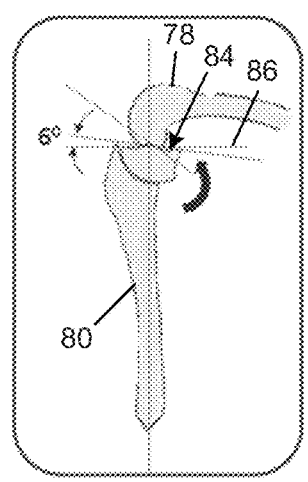

As another example, a TPLO may be performed to compensate for ruptures of the cranial cruciate ligament (for example, in dogs). A representative example of a TPLO to repair a ruptured cranial cruciate ligament is illustrated in FIGS. 12A-12C. As illustrated in FIG. 12A, the cranial cruciate ligament 76 can extend between the femur 78 and the tibia 80, and can resist advancement of the tibia in the direction indicated by arrow 82 due to force applied to the tibia by the femur. FIG. 12B illustrates forward advancement of the tibia 80 in the direction of arrow 82 due to rupture of the cranial cruciate ligament 76. In a typical example, an osteotomy using any of the saw blades disclosed herein can be made in the lateral plane on the medial side of the tibia 80 to reduce the angle θ of the tibial plateau 84 with respect to a horizontal reference plane 86, as illustrated in FIG. 12C. This can create a mechanical abutment in the caudal aspect of the knee, assisting the soft tissues in preventing the femur from sliding off the back of the tibia, mitigating the effects of a non-functional cranial cruciate ligament.

Figure 13A:
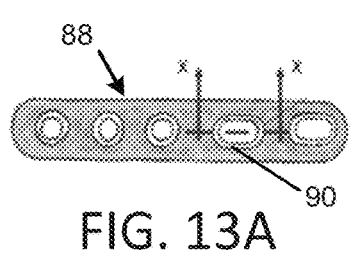
FIGS. 13A-13C illustrate operation of a representative embodiment of a compression screw hole that can be used in combination with any of the bone plates described herein.
Figure 13B:
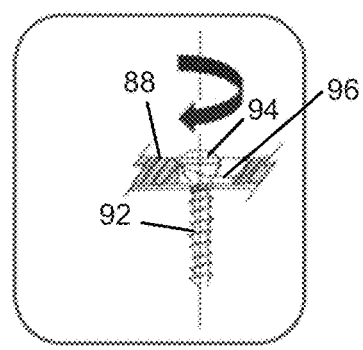
Figure 13C:
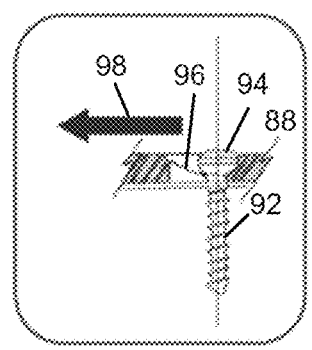

Bone plates used in association with osteotomy procedures such as the procedures described herein can provide two primary functions, namely stabilization of the osteotomy and compression of the osteotomy. In some embodiments, the bone plates described herein can incorporate one or more compression slots or compression screw holes that utilize an internal ramp within the side walls of the screw hole to apply compression to the underlying osteotomy. FIG. 13A illustrates a plan view of a representative bone plate 88 including a compression screw hole 90, and FIGS. 13B and 13C illustrate sectional views taken through the bone plate 88 along line X-X of FIG. 13A. A screw 92 can be inserted through the opening of the compression slot 90, and the head 94 of the screw can contact a ramp 96. As the screw 92 is tightened and advanced into the bone, the head of the screw applies pressure to the sloped surface of the ramp causing the bone plate to move in the direction indicated by arrow 98 shown in FIG. 13C. This can cause bone sections on opposite sides of the osteotomy to be drawn together and compressed, reducing the space between the bone sections at the osteotomy site. In some embodiments, such ramp and screw configurations can close a gap of, for example, about one (1) mm, and can provide compression (e.g., of about 10 pounds) of the bone sections against one another at the osteotomy interface. The ramp can have different configurations as, for example, an inclined plane or an inclined curvilinear surface, as shown.

Figure 14:
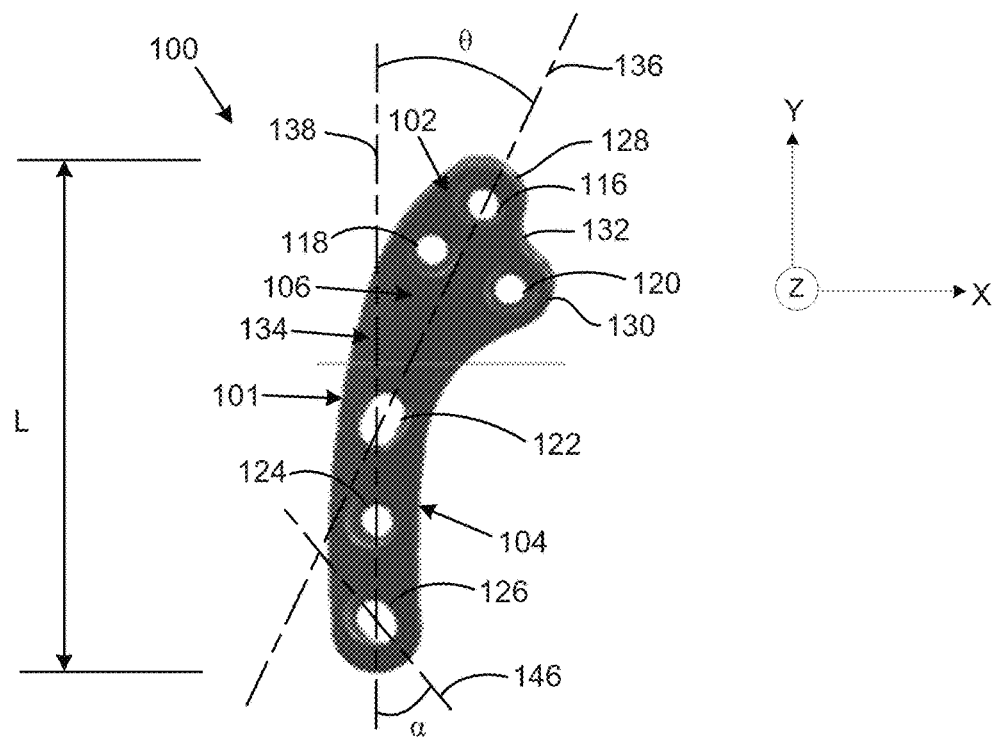
FIG. 14 is a plan view of a representative embodiment of a bone plate.

FIG. 14 illustrates a bone plate 100 having an elongated body 101 including a first end portion 102 (also referred to as a proximal end portion) and a second end portion 104 (also referred to as a distal end portion). With reference to the coordinate axes of FIG. 14, the bone plate can be curved in the X-Y plane such that the first end portion 102 is offset from the second end portion 104 in a direction along the X-axis. The first end portion 102 can have a generally curved shape, and can include a proximal lobe 128 and a distal lobe 130 separated from one another by a recessed portion 132. The first end portion can also define one or more screw holes. For example, in the illustrated embodiment the first end portion includes three screw holes 116, 118, 120 for receiving any of a variety of bone fixation screws. The screw holes 116, 118, 120 can be arranged in a generally triangular arrangement, with screw hole 116 being located on the proximal lobe 128 and the screw hole 120 being located on the distal lobe 130. In the illustrated embodiment, the screw hole 118 can be intermediate screw holes 116, 118, and offset from screw holes 116, 118 along the X-axis. In some embodiments, the location of the screw holes can be associated with optimal bone cross sections (for example, areas in which the cortical bone is thicker to aid in fixation), although it should be appreciated that the first end portion can include any suitable number of screw holes located at any suitable location.

Referring still to FIG. 14, the second end portion 104 can have a generally curved shape, and can have a width dimension that is less than a width dimension of the first end portion 102. For example, in the illustrated embodiment, the first and second end portions can be joined by a transition region generally indicated at 134, in which the width of the bone plate tapers from the relatively wider first end portion to the relatively narrower second end portion.

The second end portion can also define one or more screw holes. For example, in the illustrated embodiment the second end portion can define three screw holes 122, 124, 126, with screw holes 122 and 126 being configured as compression screw holes, although the second end portion can include any suitable number of screw holes in any suitable configuration. In the illustrated embodiment, the compression screw hole 122 can be oriented generally in the direction of the lobes 128, 130 of the first end portion 102 such that a straight line 136 extending along a longitudinal axis of the compression screw hole 122 passes through the screw hole 116 of the first end portion. In some embodiments, the straight line 136 can bisect the screw hole 116. Aligning the screw hole 116 with the longitudinal axis of the compression screw hole 122, which can be generally representative of the direction of movement of the bone plate when a screw is inserted through the compression screw hole 122, can provide increased compression between bone segments at the osteotomy site while reducing movement of the bone segments relative to one another. In some embodiments, the straight line 136 along the longitudinal axis of the screw hole 122 can define an angle θ of from about 10 degrees to about 45 degrees with a vertical reference, such as vertical line 138 bisecting the screw hole 124. In some embodiments, the angle θ can be about 25 degrees.

Referring again to the straight line 138, line 138 can extend in the direction of a length dimension L of the bone plate and can bisect the screw hole 124 of the second end portion. As illustrated in FIG. 14, each of the screw holes 116, 118, 120 of the first end portion can be offset from the straight line 138 along the X-axis. In the illustrated embodiment, each of the screw holes 116, 118, 120 of the first end portion are offset from the straight line 138 along the X-axis in the same direction (to the right in FIG. 14) such that all of the screw holes of the first end portion are on the same side of line 138 as one another. However, it should be understood that in left-handed configurations of the bone plate (see, e.g., FIG. 23), the screw holes of the first end portion can be offset from a straight line bisecting the screw hole 124 along the X-axis in the opposite direction (e.g., to the left).

In the illustrated embodiment, a longitudinal axis 146 of the compression screw hole 126 can be oriented in a direction away from the first end portion 102, as shown in FIG. 14. This can provide additional compression of the osteotomy site and rotation of the bone plate and/or of the bone segments in a counterclockwise direction upon fixation of the bone plate to the bone to improve the stability of the joint. In the illustrated embodiment, the longitudinal axis 146 of the compression screw hole 126 can define an angle α of from about 20 degrees to about 60 degrees as measured with respect to a vertical reference, such as line 138. In some embodiments, the angle α can be from about 30 degrees to about 50 degrees. In some embodiments, the angle α can be about 40 degrees.

Figure 16:
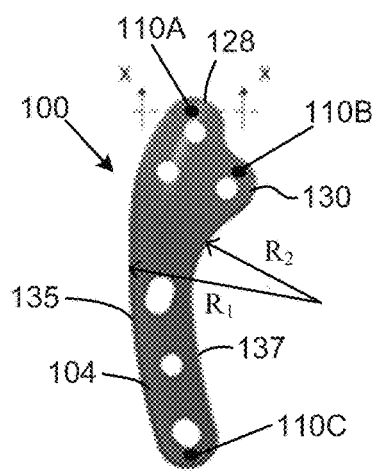
FIG. 16 is a plan view of the bone plate of FIG. 14 illustrating the location of protruding portions on the lower side of the bone plate.
Figure 23:
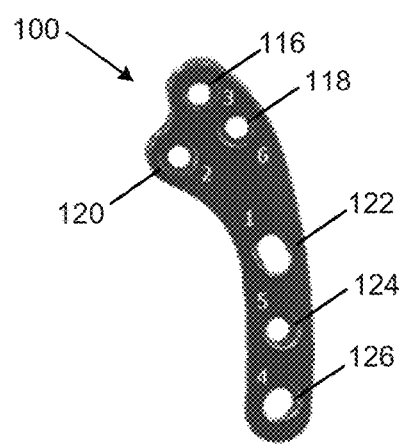
FIG. 23 illustrates a left-handed configuration of the bone plate of FIG. 14 in which the screw holes are marked with numbers indicating an exemplary order in which bone screws may be inserted into the screw holes.

In some embodiments, the bone plate 100 can have an outer plate contour (e.g., medial or lateral) such that overhang of a long bone to which the bone plate is affixed is reduced or prevented. Reducing overhang can be important to avoid soft tissue impingement, which can result in reduced range of motion and pain post-operatively. For example, in some embodiments, the ratio of the radius $R_1$ of an outer edge 135 of the bone plate and the radius $R_2$ of an inner edge 137 (see FIG. 16) can be from about 1.01 to about 4 along the length of the bone plate. The bone plate can also be made in left or right configurations to accommodate long bones on different sides of the body. For example, the bone plate illustrated in FIG. 14 is a right-handed configuration. A bone plate in a left-handed configuration is illustrated in FIG. 23.

Figure 15:
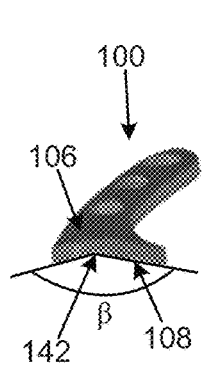
FIG. 15 is an end view of the bone plate of FIG. 14.

With reference to FIG. 15, the bone plate 100 can have an upper surface 106 and a lower surface 108, with the lower surface 108 being adjacent the surface of a bone on which the bone plate is placed. Many conventional bone plates are contoured for a fit in which a large proportion of the surface area of the bone plate is in contact with the surface of the bone to which it is affixed. In contrast, the bone plate embodiments disclosed herein can be contoured such that only a small proportion of the surface area of the bone plate is in contact with the underlying bone, while maintaining a low profile to aid with skin closure over the bone plate. For example, in the embodiment shown, the lower surface 108 is V-shaped in cross-section, in which respective angled portions of the lower surface define an angle $\beta$ of from about 90 degrees to about 170 degrees and converge at an apex 142. In some embodiments, the angle $\beta$ can be from about 120 degrees to about 170 degrees. In some embodiments, the angle $\beta$ can be about 155 degrees. By angling the lower surface 108 in the shape of a V, contact with the surface of the bone can be minimized to reduce damage to the periosteum and allow blood flow to the bone, while reducing issues with tissue closure over the bone plate. This can promote improved healing of the bone since the periosteum contains fibroblasts and progenitor cells that develop osteoblasts for maintaining and healing bone.

In some embodiments, both the upper surface 106 and the lower surface 108 can have V-shaped cross-sections. In other embodiments, the upper surface 106 can be relatively level, or rounded, while only the lower surface 108 has an angled cross-section. In some embodiments, the apex 142 can be located at or near the center of the recessed portion 132, and can be continuous along the length of the bone plate such that the entirety of the bone plate and/or the lower surface has a V-shaped cross-section. In other embodiments, the apex 142 can be proximally or distally offset from the center of the recessed portion 132, or can be continuous along only a portion of the length of the bone plate. The bone plate can also be relatively thin, such that the overlying tissue can be closed over the bone plate without undue tension.

Figure 17:
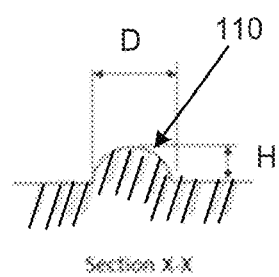
FIG. 17 is a cross-sectional view of a protruding portion taken along line X-X of FIG. 16.

In some embodiments, the lower surface 108 can include a plurality of standoffs or protrusions to further reduce contact between the bone plate and the surface of the underlying bone. For example, with reference to FIGS. 16 and 17, the lower surface can include three protrusions 110A-110C, which can provide three points of contact to establish a primary plane for reconstruction. In the representative embodiment of FIG. 16, the protrusion 110A can extend from the lower surface of the proximal lobe 128, the protrusion 110B can extend from the lower surface of the distal lobe 130, and the protrusion 110C can extend from the distal end of the second end portion 104. In this manner, when the bone plate is affixed to a bone, the protrusions 110A-110C can be the primary points of contact between the bone plate and the bone surface, thereby reducing damage to the periosteum. The protrusions 110A-110C can have a diameter D and a height dimension H, as shown in FIG. 17. In a representative embodiment, the protrusions can have a diameter of about 2 mm and a height of about 1 mm, although it should be understood that the protrusions can have any suitable size and/or shape. Additionally, it should be understood that the bone plates disclosed herein are not limited to three protrusions, but can have any suitable number of protrusions, including no protrusions, as desired.

In some embodiments, the bone plate 100 can be curved in multiple planes to maintain a geometry capable of placement within the boundaries of a bone following an osteotomy. For example, in addition to the curvature of the bone plate 100 in the X-Y plane as shown in FIG. 14, the bone plate can also be curved along the Z-axis out of the X-Y plane, as shown in FIG. 18. More specifically, in the illustrated embodiment, the first end portion 102 can be angled in the Z-direction to allow the first end portion to conform to the shape of the proximal or distal portion of a bone to which the bone plate is applied. In some embodiments, a plane defined by the lower surface 108 of the first end portion 102 can define an angle $\phi$ with a plane defined by the lower surface of the second end portion 104 of from about 5 degrees to about 40 degrees. In some embodiments, the angle $\phi$ can be from about 15 degrees to about 40 degrees. In some embodiments, the angle $\phi$ can be about 25 degrees. The angle $\phi$ may be varied from application to application, including by being bent to a desired angle by a surgeon during an osteotomy procedure, as required.

The screw holes of the bone plate can be configured for use with locking screws, non-locking screws, or combinations thereof, which can be driven into a bone to secure the plate to the bone. In some embodiments, the bone plate 100 can be used in combination with one or more locking bone screws, which can provide a locking feature in the head of the screw that locks or engages the screw with the bone plate when the screw is inserted into the bone. In some embodiments, using locking screws can help prevent the bone plate from being compressed against the bone and damaging the periosteum. Certain embodiments of locking screws that may be used in combination with the bone plates described herein are disclosed in U.S. Pat. No. 8,696,715, which is incorporated herein by reference.

FIGS. 19A and 19B illustrate the use of a representative embodiment of a locking screw 150 in combination with the bone plate 100. FIG. 19B illustrates a cross-section X-X taken through screw hole 124 of the bone plate 100 illustrated in FIG. 19A. Generally, locking screws include a head 152 and a threaded body 154 capable of fixation in cancellous or cortical bone. In some embodiments, the screw head 152 can have an external feature (for example, a partial spiral groove) to engage an internal wire (not shown) within the screw hole. This configuration can allow the screw 150 to follow multiple paths through the screw hole into the bone to address variations in the location of optimal bone between, for example, the femur, tibia, and humerus. The free movement of the wire and the diameter of the screw hole can provide for adjustment of the angle of the screw 150 relative to the longitudinal axis 156 of the hole while still providing locking between the screw and bone plate upon final tightening of the screw. This can allow a surgeon to position the screw to target desirable areas of cortical and/or cancellous bone that may not be located directly in line with the longitudinal axis of the screw hole, allowing improved fixation of the bone plate to the bone. In some embodiments, the angle of the screw can vary up to about 12 degrees from the longitudinal axis 156 of the screw hole.

This concept is applicable to all of the screw holes and compression screw holes of the bone plate, as illustrated in FIGS. 20A-20C and 21A-21B. For example, FIGS. 20A-20C illustrate exemplary regions of a tibia 160 in which screws may be inserted through screw holes 116, 118, and 120 of the first end portion 102 of the bone plate 100 in a representative TPLO procedure. In a TPLO procedure, a bone segment 162 may be cut from the proximal portion of the tibia with a radial saw blade. A circle indicated at 164 outlines the path of the osteotomy. Thus, the radially-shaped cut can have a radius substantially equal to a radius of the circle 164.

With reference to FIG. 20A, the first end portion 102 of the bone plate is located generally over the bone segment 162, while the second end portion 104 is located generally over the portion of the tibia distal to the osteotomy. FIG. 20B illustrates a plan view of the tibial head and the tibial plateau 163 above a side elevation view of the bone segment 162. Lines 1-1, 2-2, and 3-3 indicate cross-sections taken through the transverse plane of the tibia corresponding to the locations of the screw holes 116, 118, 120 on the bone segment 162, with section 1-1 being the cranial-most section and section 3-3 being the caudal-most section. The cross-sections are illustrated in FIG. 20C, where the medial aspect of the tibia is to the right in the figure. The region bounded by lines 165 and 166 illustrates the range of angles at which a bone screw can be advanced into the bone segment 162 through the screw hole 118. The region bounded by lines 167 and 168 indicates the range of angles at which a bone screw can be advanced into the bone segment through the screw hole 116, and the region bounded by lines 169 and 170 indicates the range of angles at which a bone screw can be advanced into the bone segment through the screw hole 120. In some embodiments, the screws can be advanced into the bone segment at an angle of up to about 12 degrees from the longitudinal axis of the screw hole, allowing the surgeon to target thicker and/or healthier areas of cortical bone for improved fixation, as described above.

Figure 21:
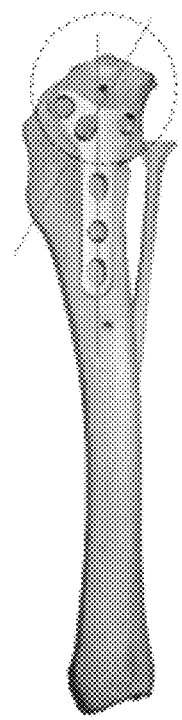
FIG. 21 illustrates a prior art bone plate.

In some embodiments, the screw hole 116 can be positioned at the geometric center 172 of the circle 164 circumscribing the osteotomy, as illustrated in FIG. 20A. Thus, the straight line 136 (see FIG. 14) bisecting the compression screw hole 122 of the second end portion 104 can also pass near or through the geometric center 172 of the osteotomy, which can improve compression applied to the osteotomy by the bone plate and reduce movement of the bone segment 162 after fixation of the bone plate 100. For example, FIG. 21 illustrates a prior art bone plate positioned over a tibia in which the geometric center of the osteotomy does not coincide with the location of a screw hole.

Figure 22A:
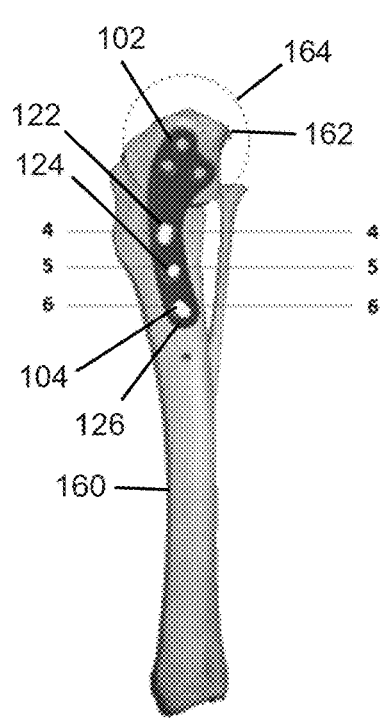
FIGS. 22A and 22B illustrate the location and range of angles at which bone screws may be inserted into a tibia through the screw holes of the second end portion of the bone plate of FIG. 14 in a TPLO procedure.
Figure 22B:
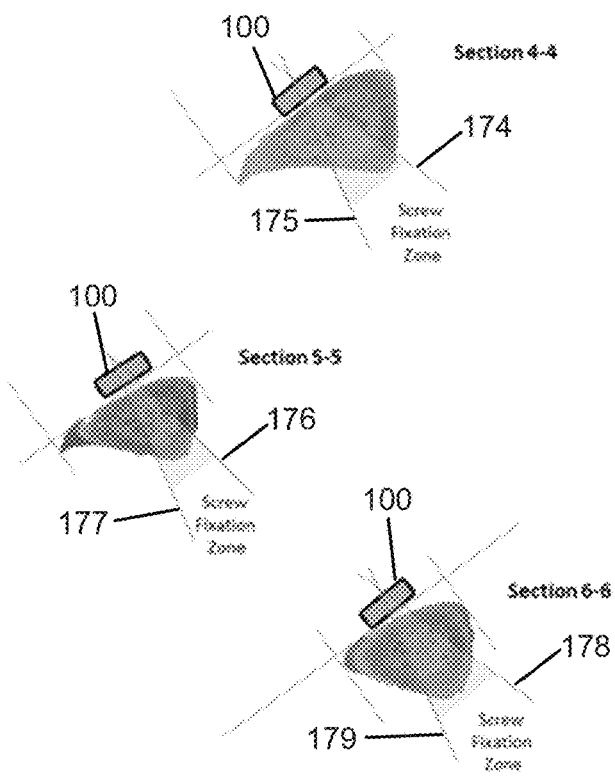

FIGS. 22A and 22B illustrate exemplary regions of the tibia 160 in which screws may be inserted through screw holes 122, 124, and 126 of the second end portion 104 of the bone plate. Lines 4-4, 5-5, and 6-6 represent cross-sections taken in respective transverse planes of the tibia 160 through the screw holes 122, 124, and 126, respectively. The cross-sections are illustrated in FIG. 22B. The region bounded by lines 174 and 175 illustrates the range of angles at which a bone screw can be advanced into the tibia through the compression screw hole 122. The region bounded by lines 176 and 177 indicate the range of angles at which a bone screw can be advanced into the tibia through the screw hole 124, and the region bounded by lines 178 and 179 indicate the range of angles at which a bone screw can be advanced into the tibia through the compression screw hole 126. The screws can be advanced into the bone segment at an angle of up to about 12 degrees from the longitudinal axis of the screw hole, as described above.

FIG. 23 illustrates a representative embodiment of the bone plate 100 in a left-handed configuration. In the bone plate of FIG. 23, the screw holes 116-126 are also numbered in accordance with an exemplary order in which bones screws can be inserted into the bone. The sequence of use of these holes can be specific to surgical techniques for particular long bone osteotomies. In some embodiments, the objective can be to establish initial fixation between the plate and the bone, then to provide compression to the osteotomy site, and then secure the bone plate and bone together. Each screw hole and compression screw hole can be marked with a number indicating its position in the sequence of screw insertion for a particular operation.

For example, in the illustrated embodiment, a screw can be inserted through compression screw hole 122 first to provide fixation of the bone plate to the proximal portion of the bone distal to the osteotomy. As shown in FIG. 23, screw hole 122 can be marked with a "1". Next, a screw can be inserted through the screw hole 120, which can be marked with a "2". A screw can then be inserted through screw hole 116, marked with a "3", to close the osteotomy gap and compress the bone segment against the remainder of the bone. A screw can then be inserted through compression screw hole 126, marked with a "4", to further compress the osteotomy and provide additional resistance to rotation of the bone segment. Next, a screw can be inserted through screw hole 124, marked with a "5", to provide further fixation of the second end portion 104 to the bone. A screw can then be inserted through screw hole 118 marked with a "6" to complete fixation of the bone plate to the bone segment, although it should be understood that insertion of bone screws into the screw holes can be performed in any suitable order depending upon the nature of procedure, etc.

Figure 24:
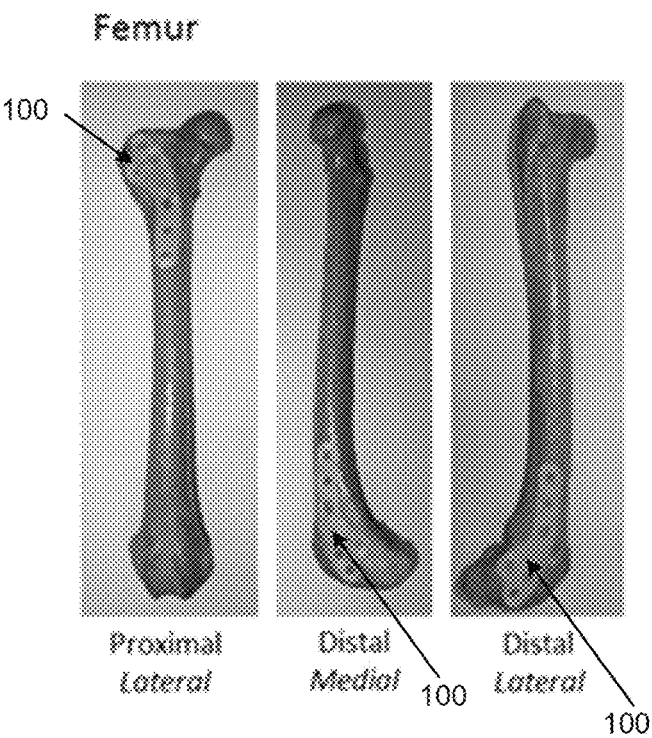
FIGS. 24-26 illustrate placement of the bone plate of FIG. 14 on various aspects of the femur, humerus, and tibia.
Figure 25:
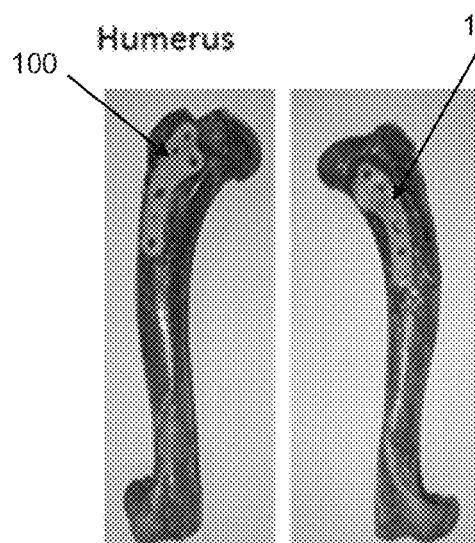
Figure 26:
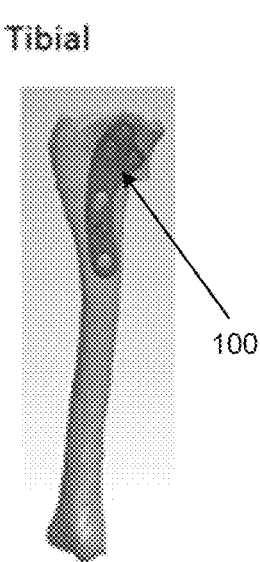

It should be understood that the bone plates and methods described herein are applicable to any long bones in canids, as well as in other mammals including felines and humans. More specifically, the ability to adjust the angle of the screws in combination with the V-shaped cross-section can allow the bone plate 100 to be used with a variety of long bones and a variety of osteotomy procedures and/or fractures of those bones. The bone plates described herein can also be used on multiple sides of the body, and at the proximal or distal ends of bones without significant modification, contrary to known bone plates. For example, FIGS. 24, 25, and 26 illustrate use of the bone plate 100 in combination with various long bones, including the proximal lateral, distal medial, and distal lateral aspects of the femur (FIG. 24), the proximal lateral and proximal medial aspects of the humerus (FIG. 25), and the proximal medial aspect of the tibia (FIG. 26).

The bone plate embodiments described herein can provide improved initial stability and improved compression at the osteotomy interface, which can yield faster healing in the desired realigned position. In some embodiments, this can be accomplished with a single bone plate family (including multiple sizes) in left and right orientations, as opposed to multiple families of plates with multiple iterations in each family.

In some embodiments, the bone plate 100 can be made of any biocompatible metal such as, for example, stainless steel, titanium, etc. In some embodiments, the bone plate 100 can comprise any of various biocompatible polymers or plastics, including polylactic acid, or other aliphatic polymers. When fabricated from polylactic acid, for example, the bone plate can be configured to be naturally resorbed or dissolved by the body after a period of time has elapsed sufficient to allow the osteotomy to heal. For example, in some embodiments the bone plate can be configured to dissolve over a period of from about 8 weeks to about 12 weeks.

FIGS. 27-31 illustrate another embodiment of a multi-directional locking screw and associated screw hole that may be used in combination with the bone plates described herein. FIGS. 27 and 28 illustrate a portion of a bone plate 200 including a screw hole 202 having threads 204 adapted to engage the head of a locking screw. The threads 204 can be, for example, female threads, and can be relatively coarse, and can be separated by groove portions 206 such that the threads are discontinuous around the inner circumference of the screw hole. The screw hole 202 can also be tapered such that the circumference of the screw hole decreases in a direction from the top surface 208 to the bottom surface 210 of the bone plate.

FIGS. 29 and 30 illustrate a representative embodiment of a locking bone screw 212 configured to be received in the screw hole 202. The screw 212 can include a head 214 and a threaded body 216. In some embodiments, the head 214 can be relatively spherical, and can include relatively coarse threads 218 (e.g., male threads) to engage the threads 204 of the screw hole 202 in the bone plate. In some embodiments, the threads of the body 216 can be have a relatively larger diameter to increase the strength of fixation to the bone.

Figures 31A, 31B, 31C:
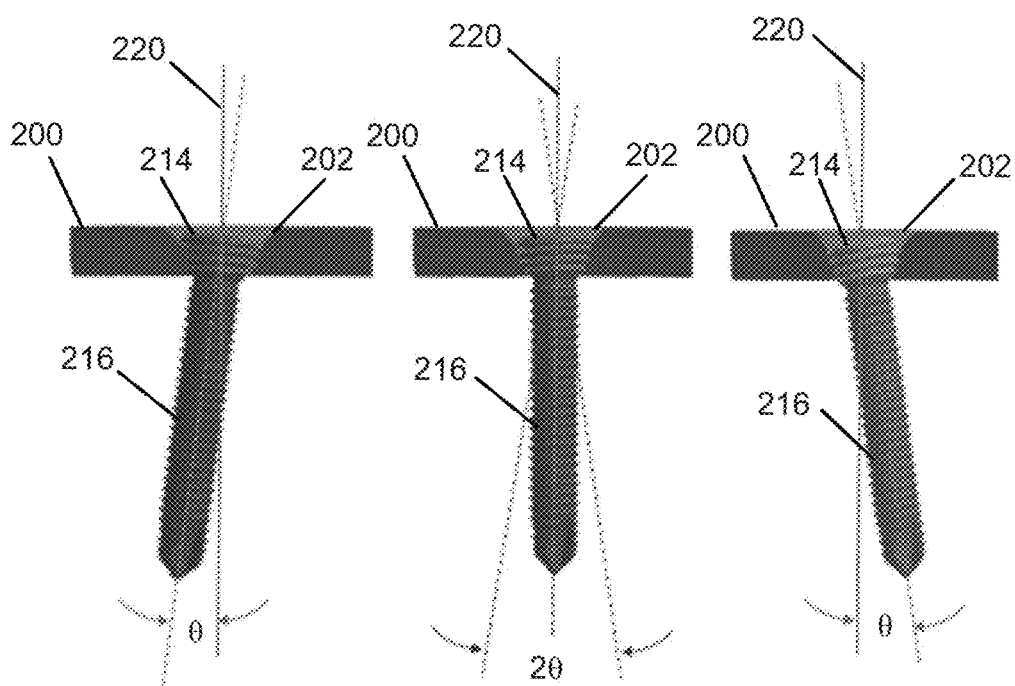
FIGS. 31A-31C illustrate engagement of the locking screw of FIG. 29 with the screw hole of FIG. 27.

With reference to FIGS. 30 and 31A-31C, the screw 212 can be movable within the screw hole 202 such that an angle θ defined by a longitudinal axis of the screw with reference to a longitudinal axis of the screw hole 202 can vary. For example, in some embodiments, the angle θ can be up to about 12 degrees with respect to the longitudinal axis of the screw hole. FIG. 31A illustrates the screw 212 angulated to the left with respect to the longitudinal axis of the screw hole, FIG. 31B illustrates the screw aligned with the longitudinal axis of the screw hole, and FIG. 31C illustrates the screw angulated to the right with respect to the longitudinal axis of the screw hole.

As used herein, the term "long bone" refers to a bone that has a length dimension greater than its diameter or width, and including, for example, the tibia, the femur, and the humerus.

As used herein, the term "proximal" refers to a direction toward the point of origin or attachment, frequently toward the center of the body.

As used herein, the term "distal" refers to a direction away from the point of origin or attachment, frequently away from the center of the body.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Some of the Figures provided herein include an orientation system that designates the X-axis, the Y-axis, and the Z-axis that are orthogonal to each other. In a majority of these Figures, the Z-axis is oriented out of the page. It should be understood that the orientation system is merely for reference and can be varied. For example, the X-axis can be switched with the Y-axis and/or the stage assembly 10 can be rotated. Moreover, these axes can alternatively be referred to as first, second, or third axes. For example, the X-axis can be referred to as the first axis, the Y-axis can be referred to as the second axis, and the Z-axis can be referred to as the third axis.

In view of the many possible embodiments to which the principles of the disclosed technology may be applied, it should be recognized that the illustrated embodiments are only preferred examples and should not be taken as limiting the scope of the disclosure. Rather, the scope of the disclosure is defined by the following claims.

What is claimed is:

1. A bone plate, comprising:
a curved elongated body including a first end portion and a second end portion, the first end portion being laterally offset relative to the second end portion;
a plurality of screw holes defined by the first end portion, the plurality of screw holes of the first end portion including a first screw hole of the first end portion;
a first screw hole defined by the second end portion;
a compression slot defined in the second end portion, the compression slot having a longitudinal axis extending in a direction toward the first end portion along an upper surface of the bone plate and passing through the first screw hole of the first end portion, the first screw hole of the first end portion being offset from the compression slot by the greatest distance along the longitudinal axis of the compression slot from among the plurality of screw holes of the first end portion;

wherein each of the screw holes of the first end portion are laterally offset from a straight line extending in a direction along a length dimension of the bone plate and bisecting the first screw hole of the second end portion;

wherein each of the screw holes of the first end portion are on the same side of the straight line as one another; and wherein the longitudinal axis of the compression slot forms an angle with the straight line.

2. The bone plate of claim 1, wherein the longitudinal axis of the compression slot bisects the first screw hole of the first end portion.

3. The bone plate of claim 1, further comprising a substantially V-shaped cross-section.

4. The bone plate of claim 3, wherein respective portions of a lower surface of the bone plate on opposite sides of an apex of the V-shaped cross-section form an angle of from about 120 degrees to about 170 degrees.

5. The bone plate of claim 1, wherein the elongated body further comprises a plurality of protruding portions extending from a lower surface of the bone plate and configured to support the elongated body above a bone.

6. The bone plate of claim 1, wherein the first end portion includes a first lobe and a second lobe, the second lobe being offset from the first lobe along the straight line in a direction toward the first screw hole of the second end portion.

7. The bone plate of claim 6, wherein the first screw hole of the first end portion is defined in the first lobe, and the second lobe defines a second screw hole of the first end portion.

8. The bone plate of claim 7, wherein the first end portion further defines a third screw hole intermediate the first and second screw holes and laterally offset from the first and second screw holes.

9. The bone plate of claim 6, further comprising a recessed portion located between the first and second lobes.

10. The bone plate of claim 1, wherein:
the first screw hole of the second end portion is a locking screw hole;
the compression slot is a first compression slot offset from the locking screw hole along the straight line in a direction toward the first end portion; and
the second end portion further defines a second compression slot on the opposite side of the locking screw hole from the first compression slot.

11. The bone plate of claim 10, wherein a longitudinal axis of the second compression slot extending along the upper surface of the bone plate defines an angle of from about 30 degrees to about 50 degrees with respect to the straight line extending along the length dimension of the bone plate and bisecting the locking screw hole of the second end portion.

12. A bone plate, comprising:
an elongated body including a first end portion and a second end portion, the elongated body defining an upper surface and a lower surface and having a V-shaped cross section, the elongated body being curved such that the first end portion is laterally offset relative to the second end portion; and
a plurality of screw holes defined by the first end portion and a plurality of screw holes defined by the second end portion, at least one of the screw holes of the second end portion being a first compression slot oriented such that a longitudinal axis of the first compression slot extending along the upper surface of the bone plate passes through a first screw hole of the first end portion;
wherein the longitudinal axis of the first compression slot forms an angle with a longitudinal axis of the bone plate; and
wherein among the plurality of screw holes of the first end portion, the first screw hole of the first end portion is offset from the first compression slot by the greatest distance along the longitudinal axis of the compression slot.

13. The bone plate of claim 12, wherein each of the screw holes of the first end portion are laterally offset from a straight line extending in a direction along a length dimension of the bone plate and bisecting a second screw hole of the second end portion, the second screw hole being offset from the first compression slot along the second end portion in a direction away from the first end portion.

14. The bone plate of claim 12, wherein respective portions of the lower surface of the bone plate on opposite sides of an apex of the V-shaped cross-section form an angle of from about 120 degrees to about 170 degrees.

15. The bone plate of claim 12, wherein the elongated body further comprises one or more protuberances extending from the lower surface and configured to support the elongated body above a bone.

16. The bone plate of claim 12, wherein the second end portion further comprises a second compression slot offset from the first compression slot along the second end portion in a direction away from the first end portion, and a longitudinal axis of the second compression slot extending along the upper surface of the bone plate defines an angle with the longitudinal axis of the first compression slot.

17. A method, comprising:
placing a bone plate on an end portion of a long bone, the bone plate including a curved elongated body having a first end portion and a second end portion, the first end portion being laterally offset relative to the second end portion, the first end portion defining a plurality of screw holes, the plurality of screw holes of the first end portion including a first screw hole of the first end portion, the second end portion defining at least one screw hole and a compression slot, the compression slot having a longitudinal axis extending along an upper surface of the bone plate in a direction toward the first end portion and passing through the first screw hole of the first end portion, the first screw hole of the first end portion being offset from the compression slot by the greatest distance along the longitudinal axis of the compression slot from among the plurality of screw holes of the first end portion, each of the screw holes of the first end portion being laterally offset from a straight line extending in a direction along a length dimension of the bone plate and bisecting the at least one screw hole of the second end portion, each of the screw holes of the first end portion being on the same side of the straight line as one another, the longitudinal axis of the compression slot forming an angle with the straight line; and
securing the bone plate to the long bone.

18. The method of claim 17, further comprising:
making a radially-shaped cut in the long bone; and
wherein placing the bone plate further comprises placing the bone plate such that a screw hole of the first end portion is positioned at the center of a circle having a radius substantially equal to a radius of the radially-shaped cut.

19. The bone plate of claim 1, wherein the straight line and the longitudinal axis of the compression slot form an angle of from about 10 ° to about 45°.

* * * * *